(12) United States Patent
Smith et al.

(10) Patent No.: US 7,236,095 B2
(45) Date of Patent: Jun. 26, 2007

(54) SOLID STATE SENSOR FOR CARBON MONOXIDE

(75) Inventors: Peter John Smith, Oxon (GB); Keith Francis Edwin Pratt, Oxon (GB)

(73) Assignee: City Technology Limited, Portsmouth (GB)

( * ) Notice: Subject to any disclaimer, the term of this patent is extended or adjusted under 35 U.S.C. 154(b) by 163 days.

(21) Appl. No.: 10/524,184

(22) PCT Filed: Oct. 8, 2003

(86) PCT No.: PCT/GB03/04322

§ 371 (c)(1),
(2), (4) Date: Feb. 10, 2005

(87) PCT Pub. No.: WO2004/034050

PCT Pub. Date: Apr. 22, 2004

(65) Prior Publication Data

US 2006/0114115 A1    Jun. 1, 2006

(30) Foreign Application Priority Data

Oct. 8, 2002  (GB) ................................. 0223350.0

(51) Int. Cl.
| G08B 17/00 | (2006.01) |
| G01N 33/97 | (2006.01) |
| G01N 7/00 | (2006.01) |
| G01N 25/18 | (2006.01) |
| G01N 21/71 | (2006.01) |

(52) U.S. Cl. ..................... 340/634; 340/632; 73/23.31; 73/31.06; 136/149; 136/153

(58) Field of Classification Search ................ 340/634, 340/632; 73/23.31, 31.06; 136/149, 153
See application file for complete search history.

(56) References Cited

U.S. PATENT DOCUMENTS

| 4,066,413 A | * | 1/1978 | Segawa et al. ................ 422/98 |
| 6,009,742 A | * | 1/2000 | Balko ......................... 73/23.31 |
| 6,046,054 A |   | 4/2000 | McGeehin et al. |

FOREIGN PATENT DOCUMENTS

| EP | 1 008 847 | 6/2000 |
| EP | 1 041 039 | 10/2000 |
| WO | WO 93/08467 | 4/1993 |
| WO | WO 95/00836 | 1/1995 |
| WO | WO 01/38867 | 5/2001 |

\* cited by examiner

*Primary Examiner*—Julie Bichngoc Lieu (57) ABSTRACT

A method of detecting a predetermined alarm condition in a combustion emission gas. The method comprises exposing to the gas a semiconductor gas sensor having a p-type mixed metal oxide semiconducting material of the first, second and/or third order transition metal series, the semiconducting material being responsive both to a change in concentration of a reducing gas in the surrounding atmosphere and to a change in concentration of oxygen in the surrounding atmosphere to exhibit a change in its electrical resistance. The resistance is monitored and an alarm signal is output if the resistance exceeds a predetermined value corresponding to the alarm condition.

15 Claims, 9 Drawing Sheets

Figure 1 : Typical combustion curves for a pre-mixed boiler

Figure 4: Dependency of sensor resistance on CO and O₂ concentrations

FIG. 5

Figure 6: Behaviour of 3 p-type MMOS sensors in a flue atmosphere. The response of an electrochemical CO sensor in a cooled extracted sample of the gas is also shown.

Figure 7: Behaviour of 3 p-type MMOS sensors in a flue atmosphere. The response of an electrochemical $O_2$ sensor in a cooled extracted sample of the gas is also shown.

SOLID STATE SENSOR FOR CARBON MONOXIDE

The invention relates to a method and system for detecting a predetermined alarm condition in a combustion emission gas.

Concern over the generation of dangerous levels of CO by malfunctioning or incorrectly adjusted domestic gas appliances has been rising in recent years. To comply with current ANSI standards in the US and ever increasing constraints on $CO_2$ emissions in the EU, there is an increasing interest in combustion or flue monitoring technology.

Figure 1:
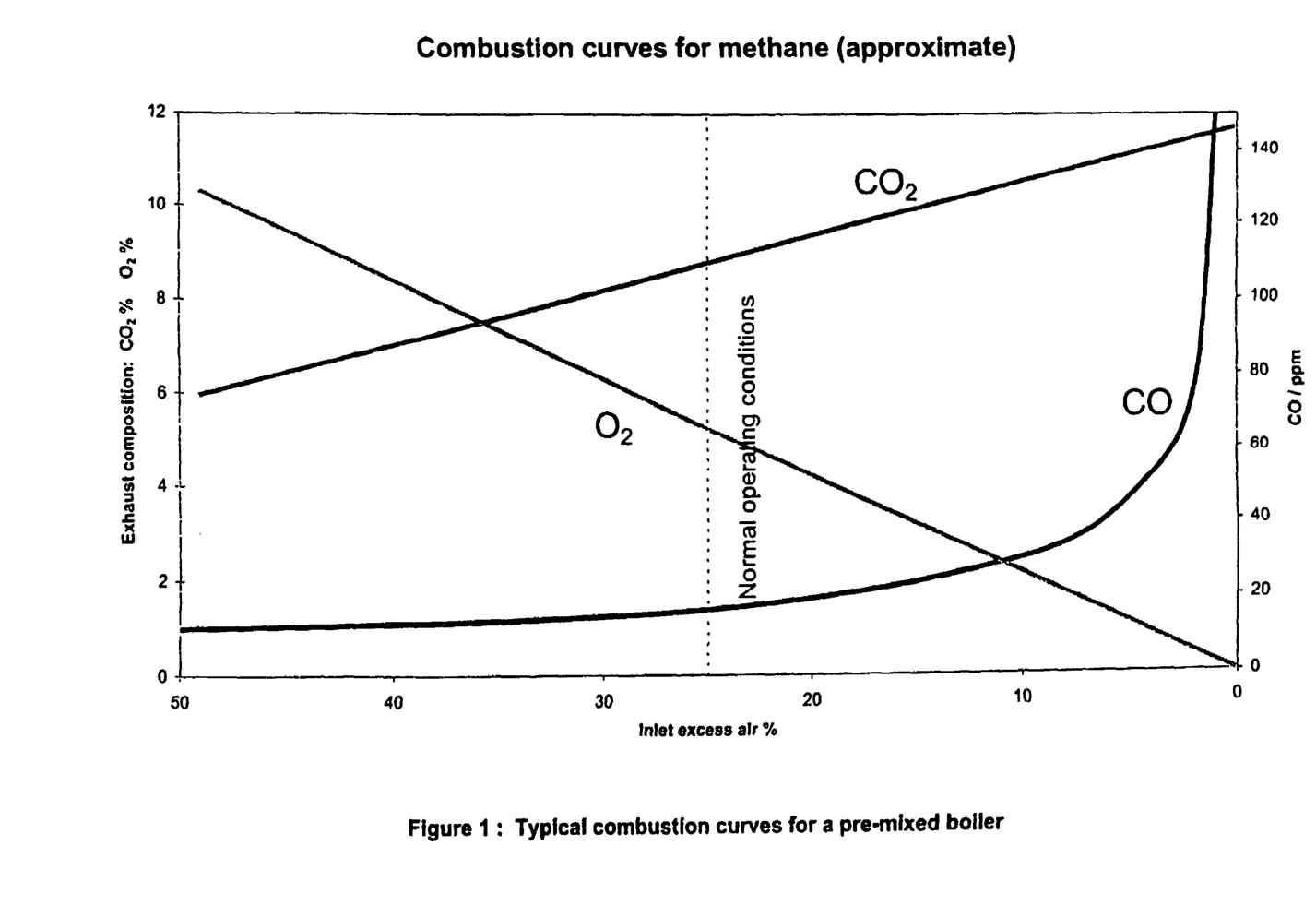
FIG. 1 illustrates typical combustion curves for a premixed boiler.

Flue gas atmospheres represent particularly aggressive conditions. Temperatures range from 40° C. to 200° C. (depending on the degree of cooling by the heat exchanger and whether or not the furnace is of a non-condensing or condensing design) while the gas itself is saturated with water vapour and creates reducing conditions due to low overall oxygen levels, typically ~5%. Other components are $CO_2$ and CO, typically at around 8% and 30 ppm respectively, with the balance being predominantly nitrogen. In the event of the flue being restricted, or of the air/fuel pre-mix not being correct, the $O_2$ level in the flue decreases. The CO level remains unchanged until the system becomes fuel-rich, whereupon it increases rapidly. FIG. 1 shows typical combustion behaviour for a pre-mixed boiler where such changes in $O_2$ and CO levels are clearly highlighted.

There are less commonly encountered situations in which significant changes in CO or $O_2$ level may occur without a major change in the concentration of the other species. Furthermore, "overgassing" may occur in which case fuel species or other partial combustion products such as $H_2$, $CH_4$ and heavier hydrocarbons can appear in the flue. A simple, reliable means of rapidly detecting either a fall in $O_2$ content or a rise in CO level is therefore required, and if such means additionally allows the detection of these other undesirable circumstances, this will confer further advantage. Although the primary application addressed here is that of a safety alarm activated in the event of malfunction, it will also be clear that one or more of these conditions may also be used to act as a control parameter to ensure safe and efficient operation of the combustion plant.

WO-A-93/08467 discloses a gas sensor for detecting more than one gas but this requires separate sensing elements.

In accordance with a first aspect of the present invention, a method of detecting a predetermined alarm condition in a combustion emission gas comprises exposing to the gas a semiconductor gas sensor having a p-type semiconducting material, the semiconducting material being responsive both to a change in concentration of a reducing gas in the surrounding atmosphere and to a change in concentration of oxygen in the surrounding atmosphere to exhibit a change in its electrical resistance; monitoring the resistance; and outputting an alarm signal if the resistance exceeds a predetermined value corresponding to the alarm condition.

In accordance with a second aspect of the present invention, a combustion emission gas alarm system comprises a semiconductor gas sensor having a p-type semiconducting material, the semiconducting material being responsive both to a change in concentration of a reducing gas in the surrounding atmosphere and to a change in concentration of oxygen in the surrounding atmosphere to exhibit a change in its electrical resistance; and apparatus for monitoring the resistance of the semiconducting material and for issuing an alarm signal if the resistance exceeds a predetermined value corresponding to an alarm condition.

Thus we use a semiconductor material which will sense oxygen, a reducing gas, or both in contrast to WO-A-93/08467 where separate sensors are required.

The invention preferably utilizes mixed metal oxides of the first, second and/or third order transition metal series. However, it is believed that metal oxides or even other materials may exhibit the required properties.

Metal oxide semiconductor sensors typically operate at elevated temperatures somewhat higher than those encountered in small flues. Because of the demanding operating conditions, and their ability to respond to a number of parameters indicating potentially dangerous situations, they represent a much more appropriate means of monitoring CO in this environment than other comparatively low cost sensors. For example, liquid electrolyte fuel cells are widely used in the industrial environment to detect dangerous levels of CO, but they are incapable of surviving for any extended period in the atmospheric conditions of the flue due to their reliance on aqueous electrolytes. Furthermore, they generally only respond significantly to a single chemical species, so separate sensors would be required to measure CO and $O_2$. Catalytic sensors, on the other hand, lack sensitivity to CO at the toxic levels of interest, are prone to poisoning of their catalysts and may give ambiguous or unreliable readings under changing oxygen levels.

Since the flue gas application is a safety critical one, where the lives of numerous persons adjacent to a malfunctioning boiler may be put in jeopardy, sensing technologies which offer fail safe operation are naturally preferred. The hot humid conditions within the flue, combined with the reducing nature of the flue gas and the potential occurrence of poisons requires that the chosen technique should be robust against corrosion and breakage of sensor connections, or loss in sensitivity due to surface poisoning. Some semiconductor materials which are widely and successfully used in other gas sensing applications are ill suited to this demanding role. The most commonly employed types are based on n-type tin oxide additionally containing precious metal catalyst additives (for example those manufactured by Figaro and other companies), but these materials fail to meet the requirements of the application for a number of reasons;

(a) Although they can respond rapidly to changing oxygen levels as required, such responses may be wholly or partially irreversible due to bulk reduction of the oxide lattice. Such effects can occur even at comparatively moderate operating temperatures.

(b) They have a limited ability to function in the presence of species which can poison the surface sites governing the gas response. Moreover, such poisoning is not necessarily detectable other than by challenging the device with a calibration gas mixture, which is an impractical requirement in a domestic situation.

(c) The increased resistance which they provide on contact failure is in opposition to the reduced resistance output which occurs on detection of increased levels of Co or reduced oxygen content. As such, it is not immediately recognised by a simple signal processing system as indicative of a dangerous condition.

(d) They are particularly prone to interference from the effects of water vapour, which can swamp the signals derived from the species of interest.

In all these respects, the n-type tin oxide device does not fail safe and as such is unsuitable for the intended application.

Although much less widely used than n-type systems, p-type semiconductor materials are known in gas sensing applications (see, for example, Chapter 4 in "Sensor Materials" by P. T. Moseley & A. J. Crocker, IoP Publishing 1996). However, their specific advantages in the demanding combustion gas emission application have not previously been realised, appreciated or quantified.

We have found that p-type mixed metal oxide semiconducting sensors of the first, second and third order transition metal series are particularly well suited for combustion gas emission, particularly flue gas, detection, for the following reasons;

(i) They exhibit excellent chemical stability in wet reducing atmospheres, due to the particularly high formation energies of the oxides.

(ii) They are resilient to the effects of typical poisons such as mercaptans and silicone sealants since they do not rely upon the presence of precious metal catalysts to generate the gas sensitive signal.

(iii) They undergo a rapid and reversible increase in resistance in response to a decrease in oxygen and/or an increase in reducing gas, e.g. CO, content of the surrounding atmosphere. The relationship between the electrical resistance of such sensors, which is the response parameter used, and the carbon monoxide and oxygen concentrations in the test atmosphere follows a relationship of the form:

$$R_G = A[O_2]^{-1/x + B[O_2]^{-1/x}}[CO]^{1/2}$$

where $R_G$ is the observed sensor resistance $[O_2]$ is the oxygen concentration $[CO]$ is the carbon monoxide concentration A, B are constants which depend on the sensor resistance under reference conditions x is a parameter which depends on the point defect chemistry of the oxide system. A typical value for x is 4.

There may be some departures to this relationship in cases where the flue temperatures are at the upper end of the range 40–200° C., resulting in the volume percent of water in the atmosphere increasing dramatically. Notwithstanding this, the overriding importance of this relationship is that it means that each undesirable condition (increased CO or decreased $O_2$) causes a change in resistance of the same sense which can be easily monitored.

(iv) They also possess a significant reversible response to other reducing species of interest.

(v) Connection faults giving rise to an apparent resistance rise can be identified as a dangerous state by a simple alarm system since the target gases will also produce a resistance increase.

Although a wide range of p-type materials are in principle suitable for such applications, the following examples are based on tests performed using standard commercial devices marketed for CO monitoring (Capteur sensor CAP07, City Technology Ltd). This design employs p-type oxides of the Cr—Ti—Mn—O system, for example as described in WO-A-01/88517, EP-A-0940673, EP-A-1135336 and EP-A-0656111. Other materials include CuO with 10% $TiO_2$ and CoO with 5% $TiO_2$.

An example of a system and method for detecting a predetermined alarm condition in a combustion emission gas will now be described with reference to the accompanying drawings, in which.

In this example, a combustion emission gas sensor is based on the use of a p-type oxide of the Cr—Ti—O system. The use of such materials in sensors is known and will be briefly described.

The sensor takes the form of a highly porous oxide layer, which is printed down onto an alumina chip. The electrodes are co-planar and located at the oxide/chip interface. A heater track is present on the backside of the chip to ensure the sensor runs "hot". This is a necessary requirement as both the interference from humidity is minimized and the speed of response is increased. MMOS sensors do not normally discriminate between different target gases. As such, considerable care is taken to ensure the microstructure of the oxide, its thickness and its running temperature are optimized to improve selectivity. In addition, selectivity is further enhanced through the use of catalytic additives to the oxide, protective coatings and various types of activated-carbon filters and on-chip catalytic oxide layers. In this example, the porous Cr—Ti—O oxide layer is coated with a catalytic oxide layer.

Figure 8:
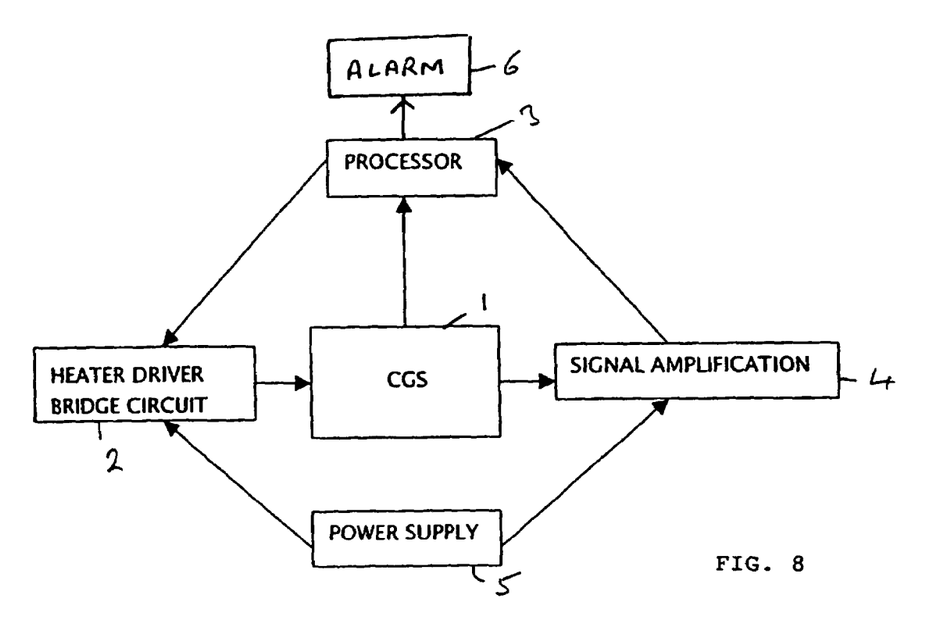
FIG. 8 is a block diagram of the system.

As can be seen in FIG. 8, the sensor 1 is connected to a heater driver bridge circuit 2 for controlling the sensor heater. An EEPROM (not shown) within the sensor 1 is connected to a microprocessor 3 while the output from the sensor 1 is connected to a simple amplification circuit 4. The EEPROM contains heater control data corresponding to the calibration temperature of the sensor. The circuit 2 and the circuit 4 are powered from a power supply 5. The processor 3 generates an output signal which, in this case, is fed to an alarm which may be a visual or audible alarm 6. In other cases, this signal could instead or additionally be fed to a control system of a boiler or other equipment generating the combustion emission gas which is being monitored.

Figure 2:
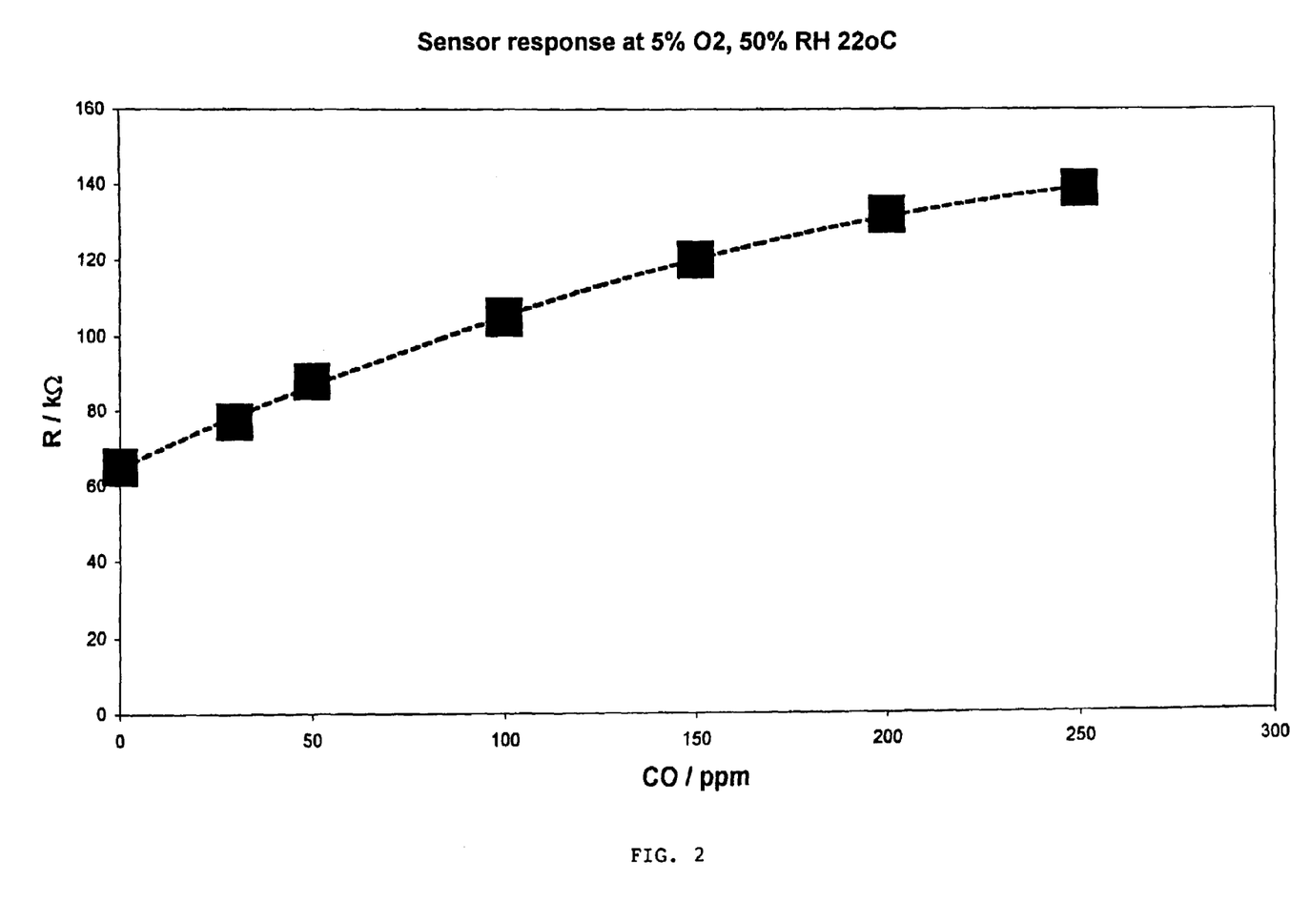
FIG. 2 illustrates the variation in sensor resistance with carbon monoxide concentration.
Figure 3:
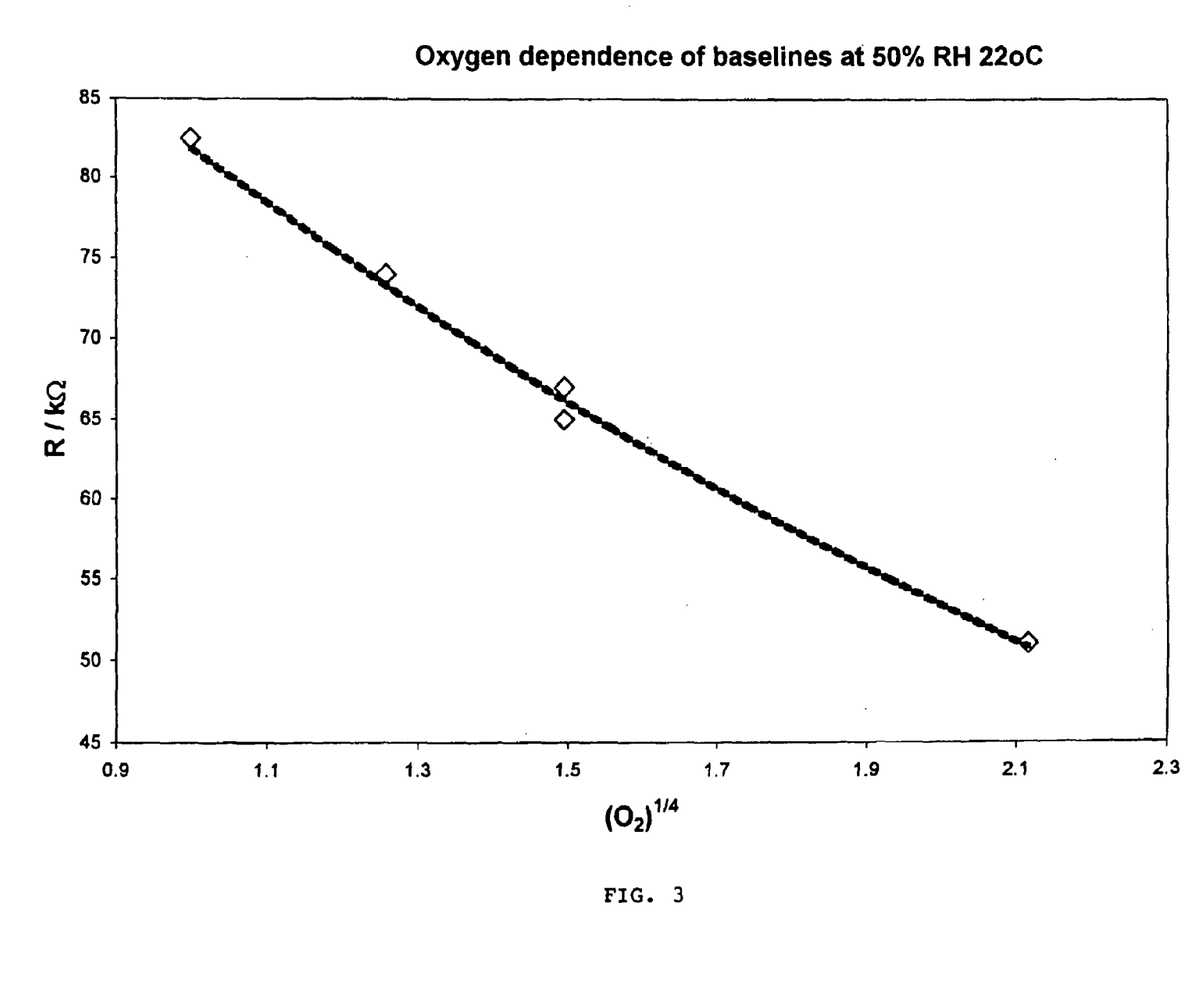
FIG. 3 illustrates the variation in sensor resistance with oxygen concentration.
Figure 4:
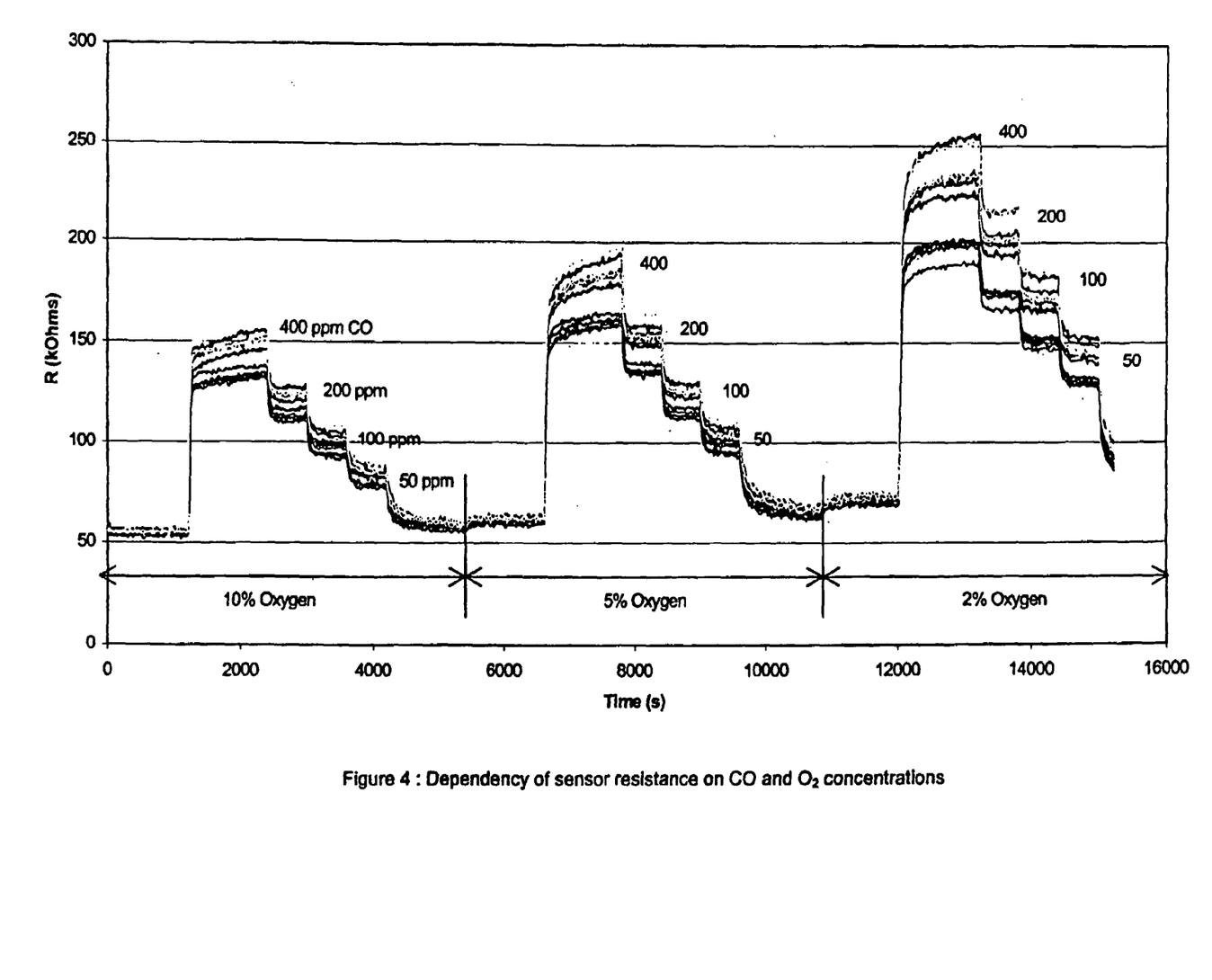
FIG. 4 illustrates the dependency of sensor resistance on carbon monoxide and oxygen concentrations for a number of different sensors.

As explained above, the sensor resistance increases with both increasing CO concentration (FIG. 2) and decreasing $O_2$ concentration (FIG. 3). Thus, whenever the air supply drops or when there is incomplete combustion for other reasons, the sensor will detect the condition as a result of this combined effect. FIG. 4 demonstrates this for a range of sensors exposed to various $CO/O_2$ combinations. It can be seen that the sensor resistance in 200 ppm CO at 10% $O_2$ is comparable to that in 100 ppm CO at 5% $O_2$ which in turn is comparable to that at <50 ppm at 2.5% $O_2$. The sensors in this example were carefully selected from a standard batch, representing the two extremes in performance, i.e. at both ends of the 95% confidence range.

Figure 5:
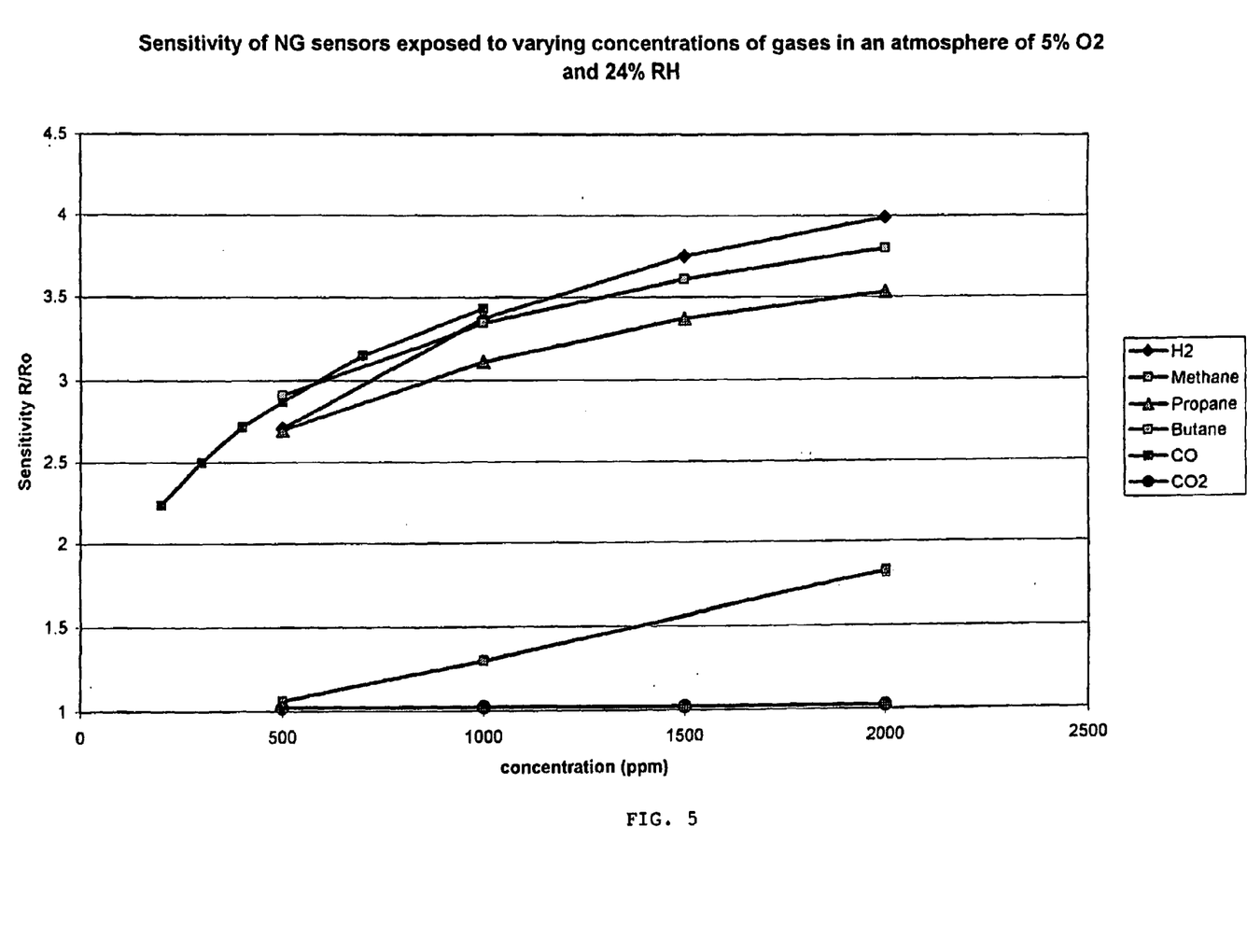
FIG. 5 illustrates the response of the sensor to a variety of different gases in 5% oxygen and 24% relative humidity.

In addition to the sensor 1 being alert to the presence of CO and varying $O_2$ concentrations, it will also respond to the presence of other relevant gases, such as $H_2$, $CH_4$, and other heavier hydrocarbon fuels. FIG. 5 shows typical responses to these gases over a range of different concentrations. The error bars represent the full range of responses for 10 sensors. A continuous atmosphere of 5% $O_2$ was maintained in this test to replicate conditions in a boiler flue whose gas is being detected.

If the sensor 1 is to be considered for use in boiler flue applications, it is important that its performance should not degrade while continuously operated over a time period commensurate with the life of the boiler or an acceptable maintenance interval. Longevity data is not as yet available for sensors operated within the flue. However, the performance of similar devices operated under typical domestic conditions (for which application the sensor was originally designed) meets the 1 year test requirements of the UL2034 standard for domestic fire detection applications.

Figure 6:
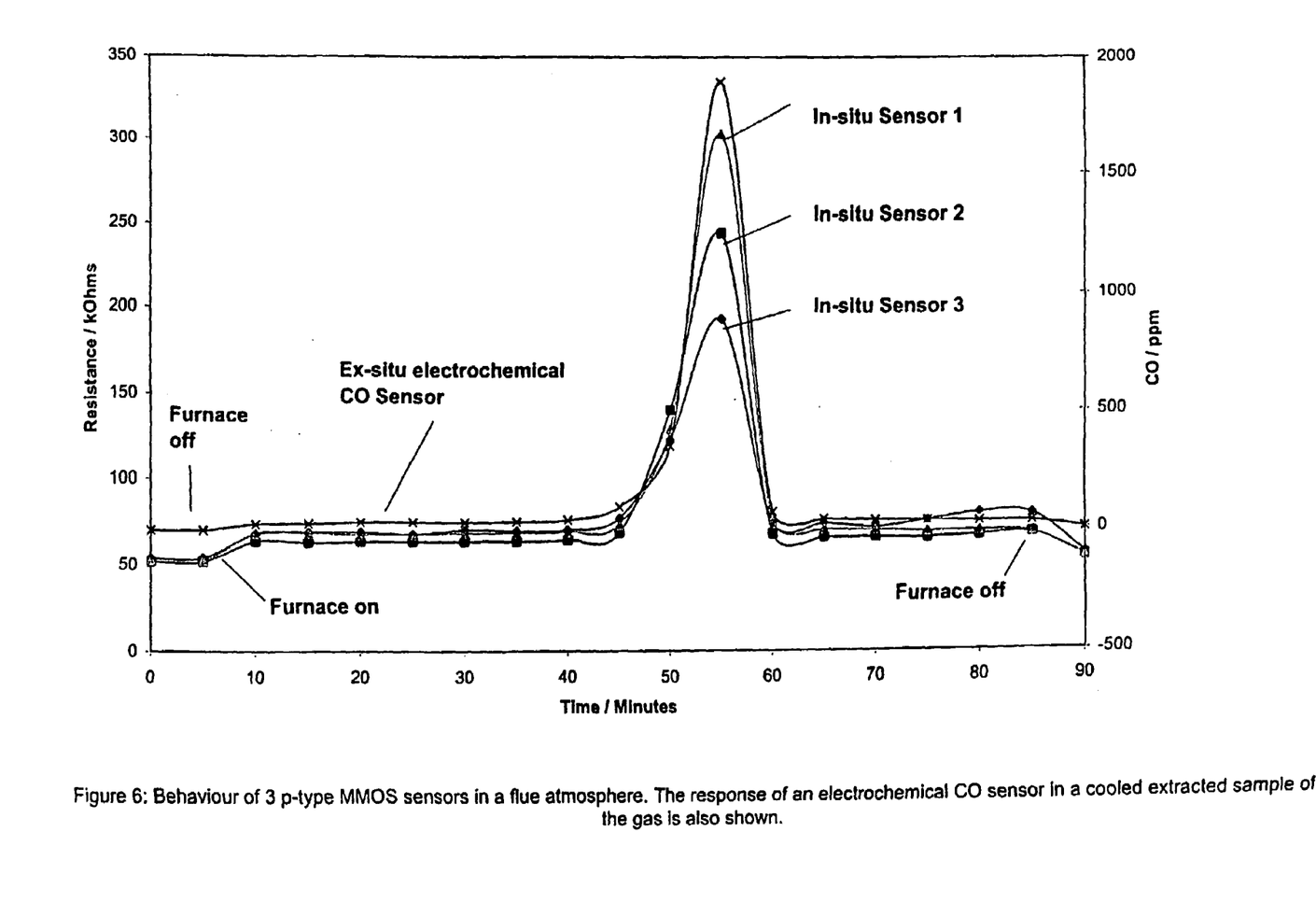
FIG. 6 illustrates the behaviour of three sensors in a flue atmosphere together with an example of the response of an electrochemical CO sensor in a cooled extracted sample of the gas.
Figure 7:
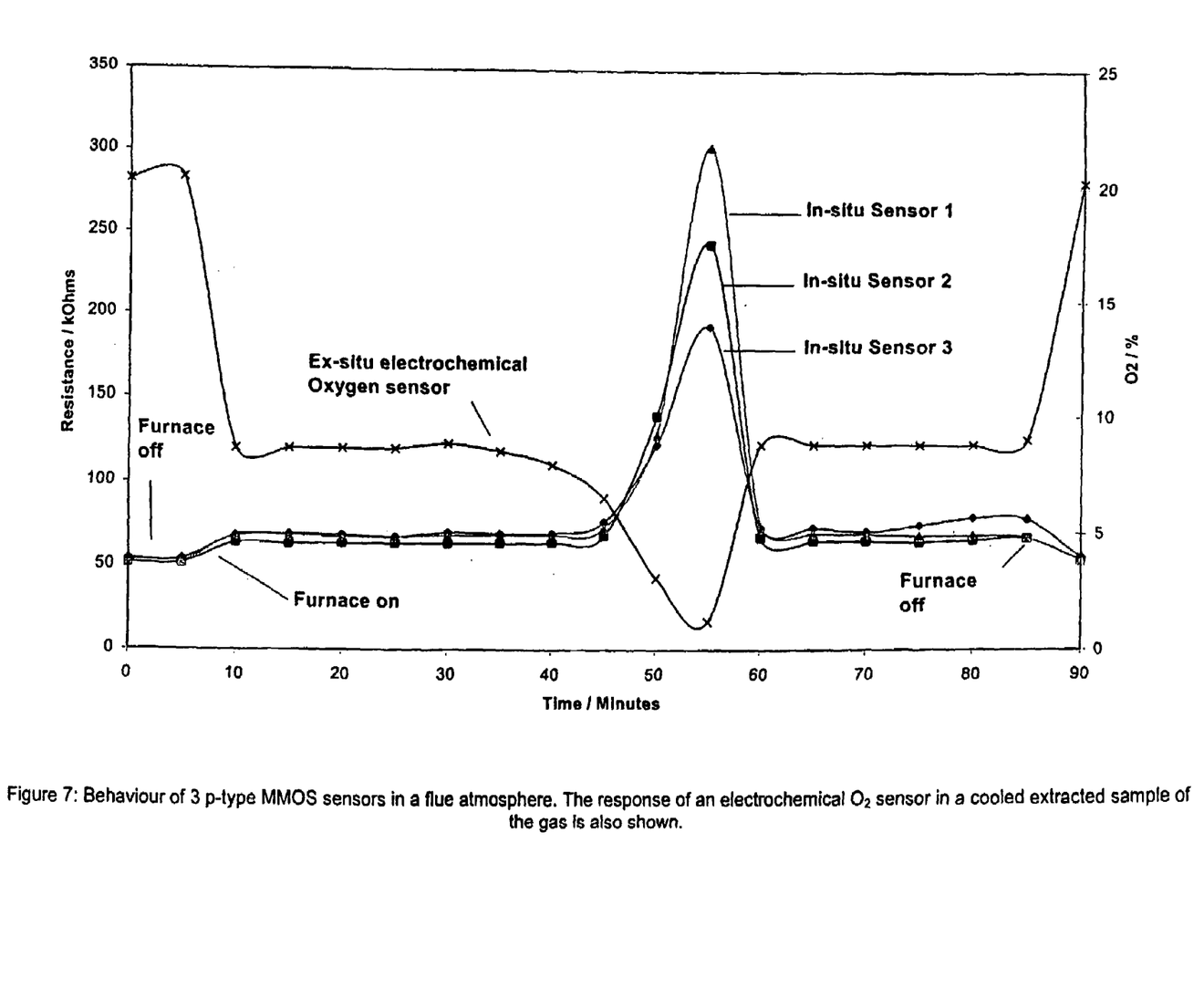
FIG. 7 is similar to FIG. 6 but in which a cooled extracted sample of the gas has been supplied to an electrochemical oxygen sensor.

FIGS. 6 and 7 show the performance of 3 p-type sensors in the flue of a condensing gas furnace. The sensors are based on sensing layers employing the Cr—Ti—O system and were set up to a resistance of 50 kohms in clean air at 50% relative humidity. At this resistance, the sensors are running at about 480–500° C. The sensors were installed in a vertical tube ducting the flue gases away from the heat exchange coils. The temperature of the flue gases at this point was 40° C. As a cross-check, a sample of the flue gas was extracted and cooled and then drawn across an electrochemical CO sensor (3F/F, City Technology Ltd) and an electrochemical $O_2$ sensor (2FO, City Technology Ltd). To create an unsafe condition, the vertical tube was restricted in stages by means of a sliding plate. It can be seen from FIGS. 6 and 7 that the p-type sensors respond to both a reduction in oxygen level and an increase in CO level. The combined effects of these two responses gives rise to a very large signal from the p-type sensors which could readily be used in conjunction with a variety of simple signal processing means to alert users of these potentially dangerous conditions.

It will be seen from the above discussion that alarm conditions caused by an increase in a toxic gas such as carbon monoxide and decrease in oxygen both cause an increase in resistance and this change in resistance is monitored by the processor 3 which will compare the monitored resistance with a predetermined threshold set such that if the threshold is exceeded, this indicates a dangerous or alarm condition. In that situation, the alarm 6 is activated.

Figure 9:
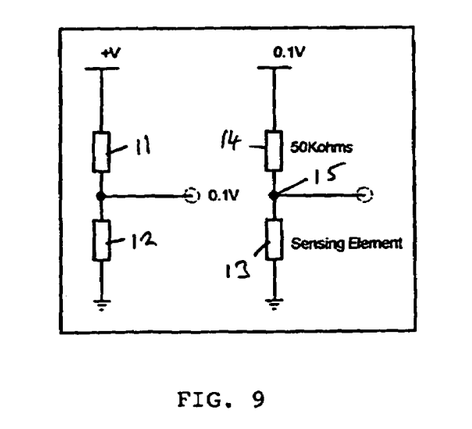
FIG. 9 illustrates how resistance of the sensor is determined.

As explained above, the resistance rises proportional to the amount of carbon monoxide (or oxygen) present and a typical resistance range is 50 KΩ (base line value with no gas present/clean air) to 150 KΩ. If the sensor is exposed to a sufficiently high current, polarization of the sensor material may occur. This requires that the sensor be measured using a low, <0.1V reference voltage. This is achieved by using a simple potential divider as shown in FIG. 9.

A voltage reference is generated and appropriate resistors 11,12 chosen to generate a voltage across the sensor of 0.1V or less. The sensing element 13 of the sensor is connected in series with a 50 KΩ resistor 14 with the 0.1V signal applied across both resistors. The output from the sensor is then taken from the point is between the two resistors. This output voltage is amplified to a sensible value, typically a gain of about 100, using the amplification circuit 4 to bring the signal with the range of the analog-to-digital converter input of the microprocessor 3.

The sensor described above uses a Cr—Ti—O material, for example Cr—Ti—Mn—O. Other suitable materials include $TiO_2$ doped CoO and CuO.

EXAMPLES

Sensors from three different p-type gas-sensitive oxide systems, Co-O (J R Stetter, J Colloid Interface Science, 65 (1978) 432, and E M Logothetis et al, Appl Phys Letters, 26 (1975) 209), Cu—O (J Gentry and T A Jones, Sensors and Actuators, 4 (1983) 581–586) and Cr—Ti—Mn—O (EP-A-1135336) which display p-type behaviour were made up. For each system, the Cr—Ti—O oxide layer in the standard City Technology CO product, Cap07, was replaced with a layer comprised of one of its oxides. For Co—O and Cu—O, $TiO_2$-doped compositions, CoO-5 wt % TiO2 and CuO-10 wt % TiO2 were used. Prior to being made into a screen-printable ink, the oxide powders were either sieved through a 32 micron sieve (Cr—Ti—Mn—O) or a 125 micron sieve (Co—Ti—O, Cu—Ti—O). The specific temperatures of sensor operation were 450° C. for both the Co—Ti—O and Cu—Ti—O examples and 400° C. for the Cr—Ti—Mn—O example, respectively.

Figure 10:
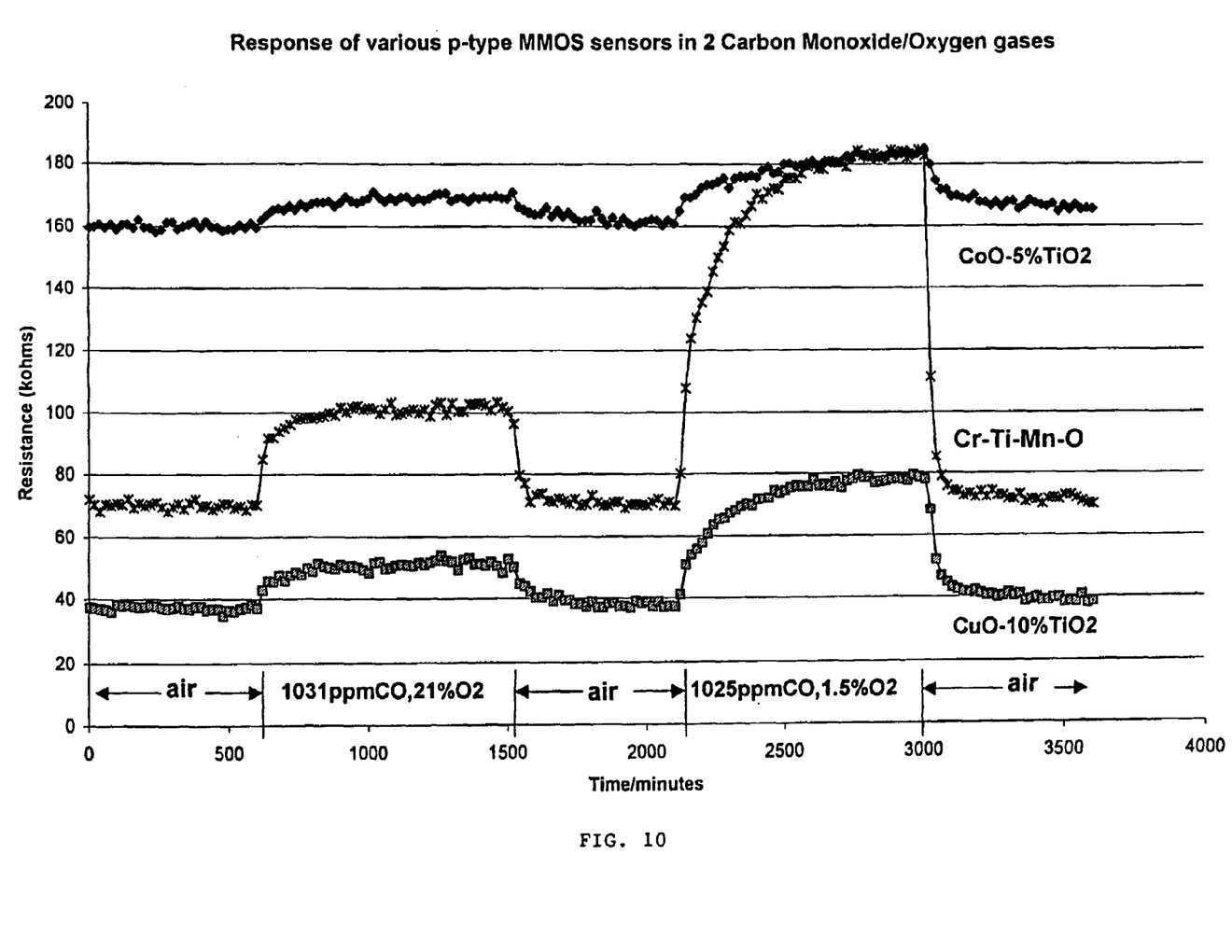
FIG. 10 illustrates the response of various p-type MMOS sensors in two carbon monoxide/oxygen gases.

The sensors were initially exposed to air at 50% relative humidity (RH), followed by sn exposure to 1031 ppm CO in 21% $O_2$ for 15 minutes, a clean-up exposure in 50% RH air, an exposure to 1025 ppm CO in 1.5% $O_2$, and a final clean-up exposure in air at 50% RH. The results shown in FIG. 10 demonstrate that these materials respond to 1031 ppm CO but in addition, the signal is further increased when exposed to a similar CO level but with a greatly reduced $O_2$ level. It is therefore evident that these systems are sensitive to atmospheric conditions in which the CO level increases and/or the $O_2$ level decreases.

The invention claimed is:

1. A method of detecting a predetermined alarm condition in a combustion emission gas, the method comprising:
    exposing to the gas a semiconductor gas sensor having a p-type semiconducting material, the semiconducting material changing electrical resistance in relation to the concentrations of oxygen and carbon monoxide in the surrounding atmosphere over at least a range of atmospheric compositions via an expression of the form $R_G = A[O_2]^{-1/x} + B[O_2]^{-1/x}[CO]^{1/2}$, where $R_G$ is the observed sensor resistance, $O_2$ is the oxygen concentration, CO is the carbon monoxide concentration, A, B are constants which depend on the sensor resistance under reference conditions, and x is a parameter which depends on the point defect chemistry of the oxide system;
    monitoring the resistance; and
    outputting an alarm signal if the resistance exceeds a predetermined value corresponding to the alarm condition.

2. The method according to claim 1, wherein the reducing gas is one of CO, H2, CH4 and higher hydrocarbons.

3. The method according to claim 1 wherein the p-type semiconductor material comprises a metal oxide.

4. The method according to claim 1 wherein the p-type semiconductor material comprises a mixed metal oxide.

5. The method according to claim 3 or claim 4, wherein the metal is of the first, second and/or third order transition metal series.

6. The method according to claim 1 wherein the p-type semiconductivity material comprises a p-type oxide of the CrTi-0 system.

7. The method according to claim 1 wherein the p-type semiconductivity material comprises a p-type Cr-Ti-Mn-Co system, CuO with T'02 or Coo with K02.

8. The method according to claim 1 wherein the combustion emission gas is a flue gas.

9. A combustion emission gas alarm system comprising:
   a semiconductor gas sensor having a p-type semiconducting material, the semiconducting material changing electrical resistance in relation to the concentration of oxygen and carbon monoxide in the surrounding atmosphere over at least a range of atmospheric compositions via an expression of the form $$R_G = A[O_2]^{-1/x} + B[O_2]^{-1/x}[CO]^{1/2},$$

where $R_G$ is the observed sensor resistance, $O_2$ is the oxygen concentration, CO is the carbon monoxide concentration, A, B are constants which depend on the sensor resistance under reference conditions, and x is a parameter which depends on the point defect chemistry of the oxide system; and
   apparatus for monitoring the resistance of the semiconducting material and issuing an alarm signal if the resistance exceeds a predetermined value corresponding to an alarm condition.

10. The system according to claim 9, wherein the p-type semiconducting material comprises a metal oxide.

11. The system according to claim 9, wherein the p-type semiconducting material comprises a mixed metal oxide.

12. The system according to claim 10 or claim 11, wherein the metal is of the first, second and/or third order transition metal series.

13. The system according to claim 9 wherein the p-type semiconducting material comprises a p-type oxide of the Cr-i-O system.

14. The system according to claim 9, wherein the p-type semiconducting material comprises a p-type CuO with $TiO_2$ or CoO with $TiO_2$.

15. The system according to claim 9 wherein the system is mounted to or adjacent to a flue gas outlet so as to expose the sensor to the flue gas.

* * * * *